United States Patent
Lee et al.

(10) Patent No.: US 10,378,031 B2
(45) Date of Patent: Aug. 13, 2019

(54) O-ACETYLHOMOSERINE SULFHYDRYLASE VARIANT AND METHOD FOR PRODUCING L-METHIONINE USING SAME

(71) Applicant: CJ CHEILJEDANG CORPORATION, Seoul (KR)

(72) Inventors: Imsang Lee, Yongin-si (KR); Sung Kwang Son, Seoul (KR); Hyeryun Yoo, Suwon-si (KR); Jae Hee Lee, Seoul (KR); Joo Hee Lee, Suwon-si (KR); Jin Sook Chang, Suwon-si (KR); Jin-Geun Choi, Seoul (KR); So Young Kim, Gwacheon-si (KR); Yong Uk Shin, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/765,577

(22) PCT Filed: Oct. 13, 2016

(86) PCT No.: PCT/KR2016/011503
§ 371 (c)(1),
(2) Date: Apr. 3, 2018

(87) PCT Pub. No.: WO2017/065529
PCT Pub. Date: Apr. 20, 2017

(65) Prior Publication Data
US 2018/0355389 A1    Dec. 13, 2018

(30) Foreign Application Priority Data
Oct. 13, 2015  (KR) ................. 10-2015-0143035

(51) Int. Cl.
*C12N 9/10* (2006.01)
*C12N 15/70* (2006.01)
*C12P 13/12* (2006.01)

(52) U.S. Cl.
CPC ............... *C12P 13/12* (2013.01); *C12N 9/10* (2013.01); *C12N 15/70* (2013.01)

(58) Field of Classification Search
CPC . C12P 13/12; C12N 15/8243; C12N 15/8253; C12N 15/70
See application file for complete search history.

(56) References Cited

U.S. PATENT DOCUMENTS 7,611,873 B1    11/2009   Usuda et al.

FOREIGN PATENT DOCUMENTS

| EP | 2657249 A2 | 10/2013 |
|----|------------|---------|
| JP | 2000-139471 A | 5/2000 |
| JP | 2014-506129 A | 3/2014 |
| KR | 10-2008-0102123 A | 4/2010 |
| KR | 10-2009-0106365 A | 4/2012 |
| KR | 10-1250651 B1 | 4/2013 |
| WO | 2008-013432 A1 | 1/2008 |
| WO | 2010-098629 A2 | 9/2010 |

OTHER PUBLICATIONS

International Search Report and Written Opinion in International Patent Application No. PCT/KR2016/011503, dated Jan. 31, 2017.
Izsvak et al., "Sleeping Beauty, a Wide Host-range Transposon Vector for Genetic Transformation in Vertebrates," J. Mol. Biol., 302, pp. 93-102 (2000).
NCBI, Genbank accession No. ACM00019.1. [Cited in International Search Report and Written Opinion in International Patent Application No. PCT/KR2016/011503, dated Jan. 31, 2017].

*Primary Examiner* — Kagnew H Gebreyesus
(74) *Attorney, Agent, or Firm* — Venable LLP; Keith G. Haddaway; Miguel A. Lopez (57) ABSTRACT

The present disclosure relates to a novel O-acetylhomoserine sulfhydrylase variant, a polynucleotide encoding the same, a vector comprising the polynucleotide, a strain capable of expressing the variant, and a method for producing L-methionine using the variant.

7 Claims, 1 Drawing Sheet
Specification includes a Sequence Listing.

AA Row 1: cell lysate
BB Rows 2-6: MonoQ eluted fraction
CC Row 7: MonoQ concentrated solution of eluted fraction
DD Rows 8-10: Superdex 75pg eluted fraction
EE R. spheroid MetZ

O-ACETYLHOMOSERINE SULFHYDRYLASE VARIANT AND METHOD FOR PRODUCING L-METHIONINE USING SAME

SEQUENCE LISTING

The instant application contains a Sequence Listing which has been submitted electronically in ASCII format and is hereby incorporated by reference in its entirety. Said ASCII copy, created on Aug. 15, 2018, is named Sequence Listing for US 15765577.txt and is 10,843 bytes in size.

TECHNICAL FIELD

The present disclosure relates to a novel O-acetylhomoserine sulfhydrylase variant, a polynucleotide encoding the same, a vector containing the polynucleotide, a strain capable of expressing the variant, and a method for producing L-methionine using the variant.

BACKGROUND ART

L-methionine, an essential amino acid in a living body, has been used as feed, infusion, a medicinal raw material such as a synthetic raw material for pharmaceutical drugs, and food additives. Methionine is an important amino acid involved in transmethylation in vivo and has a role of providing sulfur.

For the chemical synthesis of methionine, a method to hydrolyze 5-(β-methylmercaptoethyl)-hydantoin to produce methionine in the form of a mixture of L-type and D-type is mainly used. However, the chemical synthesis results in a production of methionine in the form of a mixture of L-type and D-type. Meanwhile, L-methionine may be selectively produced using a biological method, in which L-methionine is produced by direct fermentation using a microorganism or by a two-step process (International Patent Publication No. WO 2008/013432). Specifically, the two-step process consists of a process for producing L-methionine precursor by fermentation and a process for converting the L-methionine precursor to L-methionine by an enzyme. The two-step process can selectively produce only L-methionine and further produce simultaneously organic acids, more specifically succinic acid or acetic acid as byproducts by the same reaction.

The L-methionine precursor may include O-acetylhomoserine and O-succinylhomoserine, and the enzymes used in the conversion process may include O-succinylhomoserine sulfhydrylase and O-acetylhomoserine sulfhydrylase. To maximize L-methionine production by the two-step process, it is necessary to secure the maximal amount of fermented O-acyl homoserine, which is a precursor of L-methionine. Simultaneously, the enzymes used for enzyme conversion to produce L-methionine must have high conversion activity, exhibit overexpression in microorganisms, and maintain a high reaction rate at high concentrations of O-acyl homoserine. Additionally, the enzymes must have low activity-inhibition at a time point when the final product (i.e., L-methionine and organic acid) is accumulated at high concentration and have thermal stability not to lose their activity during reactions. In this regard, KR Patent No. 10-1250651 discloses O-acetylhomoserine sulfhydrylase derived from *Rhodobacter sphaeroides*, which has higher thermal stability than O-acetylhomoserine sulfhydrylases derived from microorganisms other than *Rhodobacter sphaeroides*, and is thus newly available for use in the two-step process. However, there is still a need to develop an enzyme, which has high conversion activity for use in the two-step process, etc. and low activity-inhibition at a time point when the final products are accumulated.

DISCLOSURE

Technical Problem

The inventors of the present disclosure have made efforts to develop O-acetylhomoserine sulfhydrylase as an enzyme with improved conversion. As a result, they have confirmed that modified polypeptides, in which the 196$^{th}$ amino acid of the *Rhodobacter sphaeroides*-derived O-acetylhomoserine sulfhydrylase is modified with an amino acid other than valine, have higher conversion and stability compared to wild-type O-acetylhomoserine sulfhydrylase, thereby completing the present disclosure.

Technical Solution

An object of the present disclosure is to provide an O-acetylhomoserine sulfhydrylase variant.

Another object of the present disclosure is to provide a polynucleotide encoding the variant.

Still another object of the present disclosure is to provide a vector including the polynucleotide.

Still another object of the present disclosure is to provide a microorganism producing the O-acetylhomoserine sulfhydrylase variant.

Still another object of the present disclosure is to provide a method for producing methionine using the O-acetylhomoserine sulfhydrylase variant.

Advantageous Effects of the Invention

The modified polypeptides of the present disclosure having O-acetylhomoserine sulfhydrylase activity are modified polypeptides which are provided with all of the requirements, such as high activity for use as an industrial conversion enzyme, high conversion rate, possibility of overexpression in *E. coli*, low activity-inhibition at a time point when the final product is accumulated, maintenance of thermal stability, etc. Accordingly, the modified polypeptides of the present disclosure are advantageous in that they can be used for rapid and highly efficient production of L-methionine along with acetic acid as a byproduct.

BEST MODE

To achieve the above objects, an aspect of the present disclosure may provide a novel modified polypeptide having O-acetylhomoserine sulfhydrylase activity. The modified polypeptide may be a modified polypeptide having O-acetylhomoserine sulfhydrylase activity, in which the 196$^{th}$ amino acid from the N-terminus of an amino acid sequence of O-acetylhomoserine sulfhydrylase derived from *Rhodobacter sphaeroides*, and specifically the 196$^{th}$ amino acid from the N-terminus of the polypeptide described by the amino acid sequence of SEQ ID NO: 1, is substituted with an amino acid other than valine. More specifically, the modified polypeptide may be a variant in which the 196$^{th}$ amino acid from the N-terminus (i.e., valine) is substituted with threonine. Specifically, the modified polypeptide having O-acetylhomoserine sulfhydrylase activity may be a modified polypeptide having the amino acid sequence of SEQ ID NO: 3, but the modified polypeptide is not limited thereto.

The modified polypeptide as such has an enhanced O-acetylhomoserine sulfhydrylase activity compared to the polypeptide of SEQ ID NO: 1 having the O-acetylhomoserine sulfhydrylase activity.

As used herein, the term "modification" or "variant" refers to a culture product or individual subject which genetically or non-genetically exhibits a stable phenotypic change, and specifically, refers to a variant in which an amino acid of O-acetylhomoserine sulfhydrylase derived from *Rhodobacter sphaeroides* is modified and is thus able to efficiently increase its activity compared to that of its wild-type. The sequence of such a variant may include a polypeptide having a homology of at least 80%, at least 90%, at least 95%, at least 96%, at least 97%, at least 98%, or at least 99% to the above modified polypeptide. Specifically, the modified polypeptide of the present disclosure having a O-acetylhomoserine sulfhydrylase activity may include the polypeptide of SEQ ID NO: 3 and a polypeptide which has a homology to the sequence of SEQ ID NO: 3 of at least 80%, at least 90%, at least 95%, at least 96%, at least 97%, at least 98%, or at least 99%. Additionally, it is obvious that any enzyme variant having an amino acid sequence with deletion, modification, substitution, or addition in part of the sequence while retaining the modification of the 196$^{th}$ amino acid (i.e., a particular position) to an amino acid other than valine, can also be included in the scope of the present disclosure, as long as the amino acid sequence has a homology described above and has an effect corresponding to that of the enzyme. Additionally, any polypeptide, which is encoded by a probe that can be prepared from known gene sequences (e.g., polynucleotide that can be hybridized under stringent conditions with complementary sequences to the entirety or part of the nucleotide sequence encoding the polypeptide) and has the O-acetylhomoserine sulfhydrylase activity, can also be included without limitation in the scope of the present disclosure.

As used herein, the term "stringent conditions" means conditions which permit specific hybridization between polynucleotides. Such conditions rely on length and the degree of complementarity of the polynucleotides, and the related parameters are well-known in the art, and are specifically described in references (e.g., J. Sambrook et al., supra). For example, the conditions may include performing hybridization between genes having a high homology, a homology of 80% or higher, specifically 90% or higher, more specifically 95% or higher, even more specifically 97% or higher, and most specifically 99% or higher, while not performing hybridization between genes having a homology of lower than the above homologies; or to perform hybridization once, specifically two or three times, under conventional washing conditions for Southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

The probes used in the hybridization may be part of the complementary sequences of the nucleotide sequences. These probes may be prepared by PCR using oligonucleotides prepared based on known sequences as primers and gene fragments containing the nucleotide sequences as a template. Additionally, an ordinary person skilled in the art may adjust the temperature and salt concentration of wash solutions as needed depending on factors such as the length of the probes.

As used herein, the term "homology" refers to a percentage of identity between two polynucleotide or polypeptide moieties. The homology between sequences from one moiety to another may be determined by a known technique in the art. For example, homology may be determined by directly aligning sequence information such as parameters including score, identity, similarity, etc., (e.g., BLAST 2.0) between two polynucleotide molecules or two polypeptide molecules using an easily available computer program that is capable of aligning sequence information. Additionally, the homology between polynucleotides may be determined by hybridizing the polynucleotides under conditions in which the polynucleotides cam form a stable double strand between homologous regions followed by decomposing them using a single-strand-specific nuclease so as to determine the size of the decomposed fragments.

The polypeptide described by the amino acid sequence of SEQ ID NO: 1 may be a wild-type polypeptide having an activity of O-acetylhomoserine sulfhydrylase derived from *Rhodobacter sphaeroides*. The polypeptide having an activity of O-acetylhomoserine sulfhydrylase of SEQ ID NO: 1 has higher thermal stability compared to peptides derived from other microorganisms (e.g., *Hyphomonas neptunium*, etc.). Therefore, it is obvious that the modified polypeptide of the present disclosure, in which an amino acid substitution is introduced to the polypeptide having the activity of O-acetylhomoserine sulfhydrylase of SEQ ID NO: 1, will also have an advantage in that it has high thermal stability.

As used herein, the term "O-acetylhomoserine" refers to the first specific intermediate in the methionine biosynthesis that can be observed in microorganisms, and it can be produced by catalysis using homoserine acetyltransferase in L-homoserine and acetyl-CoA at the junction of threonine biosyntehsis.

As used herein, the term "precursor" refers to a metabolite that is part of the methionine-specific metabolic pathway produced by L-methionine precursor-producing strains or those derived from the metabolite thereof. In the present disclosure, examples of the L-methionine precursor may be O-succinylhomoserine or O-acetylhomoserine, but is not limited thereto.

As used herein, the term "L-methionine precursor-producing strain" refers to a prokaryotic or eukaryotic microorganism strain which, being capable of producing an L-methionine precursor in vivo, is able to accumulate the L-methionine precursor. For example, the L-methionine precursor-producing strain may include microorganism strains that belong to the genus *Escherichia*, the genus *Erwinia*, the genus *Serratia*, the genus *Providencia*, the genus *Corynebacterium*, the genus *Pseudomonas*, the genus *Leptospira*, the genus *Salmonella*, the genus *Brevibacterium*, the genus *Hyphomononas*, the genus *Chromobacterium*, the genus *Nocardia*, or those microorganisms that belong to fungi or yeasts. Specifically, the strain may be a microorganism of the genus *Escherichia*, the genus *Corynebacterium*, or the genus *Leptospira*, and more specifically a microorganism of the genus *Escherichia* (e.g., *Escherichia coli*), but the strain is not limited thereto.

Another aspect of the present disclosure provides a polynucleotide encoding the modified polypeptide.

The polynucleotide may be a polynucleotide which encodes a modified polypeptide having O-acetylhomoserine sulfhydrylase activity, in which the 196$^{th}$ amino acid from the N-terminus of the polypeptide represented by the amino acid sequence of SEQ ID NO: 1 (i.e., valine) is substituted with a different amino acid. For example, the polynucleotide may be a polynucleotide having the nucleotide sequence of SEQ ID NO: 4, but the nucleotide sequence is not limited thereto. Additionally, the polynucleotide may be a polynucleotide having a homology of at least 80%, at least 90%, at least 95%, at least 97%, or at least 99% to the sequence of SEQ ID NO: 4. Additionally, based on codon degeneracy, it is obvious that any nucleotide sequence encoding polypeptides, which can hybridize under stringent conditions with nucleic acids (which consist of nucleotide sequences complementary to polynucleotides that can be translated into the modified polypeptide as well as to the nucleotide sequence of SEQ ID NO: 4) and have an activity of O-acetylhomoserine sulfhydrylase, can also be included in the scope of the present disclosure.

Still another aspect of the present disclosure provides a vector which includes a polynucleotide encoding the modified polypeptide. The vector may be in a form operably linked to the polynucleotide.

As used herein, the term "operably linked" refers to an operable linkage between a control sequence for nucleotide expression and a nucleotide sequence encoding a target protein for performing its general functions, and this can affect the expression of the nucleotide sequence being encoded. Operable linkage with a vector may be prepared using a genetic recombination technique known in the art, and site-specific DNA cleavage and ligation may be performed using a restriction enzyme, a ligase, etc. known in the art.

As used herein, the term "vector" refers to any mediator for cloning and/or transfer of nucleotides into a host cell. A vector may be a replicon to enable the replication of a DNA fragment bound by another DNA fragment. The term "replicon" refers to any genetic unit acting as a self-replicating unit for DNA replication in vivo, i.e., being replicable by self-regulation (e.g., plasmids, phages, cosmids, chromosomes, viruses, etc.). The term "vector" may include viral and non-viral mediators for introducing nucleotides into a host cell in vitro, ex vivo, or in vivo, and also may include a mini-spherical DNA. For example, the vector may be a plasmid without any bacterial DNA sequence. The term "vector" may include a transposon such as Sleeping Beauty (Izsvak et al., *J. Mol. Biol.* 302: 93 to 102 (2000)), or an artificial chromosome. Examples of the conventional vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vector that can be used in the present application is not particularly limited but any known expression vector may be used.

Additionally, the vector may be a recombinant vector which further includes various antibiotic resistance genes.

As used herein, the term "antibiotic resistance gene" refers to a gene having resistance to antibiotics, and the cells including this gene can survive even in an environment treated with the corresponding antibiotic. Therefore, the antibiotic resistance gene can be effectively used as a selection marker for a large-scale production of plasmids in *E. coli*. In the present disclosure, the antibiotic resistance gene is not a factor that significantly affects the expression efficiency according to an optimal combination of vectors which is core technology of the present disclosure, and thus any common antibiotic resistance gene can be used as a selection marker without limitation. For example, resistance genes against ampicilin, tetracyclin, kanamycin, chloramphenicol, streptomycin, or neomycin, etc. can be used.

Still another aspect of the present disclosure provides a microorganism producing O-acetylhomoserine sulfhydrylase, which can express a modified polypeptide having an activity of O-acetylhomoserine sulfhydrylase or includes the vector including a polynucleotide encoding the modified polypeptide, and specifically, a microorganism of the genus *Escherichia* producing O-acetylhomoserine sulfhydrylase, in which the 196$^{th}$ amino acid from the N-terminus of the polypeptide represented by the amino acid sequence of SEQ ID NO: 1, valine, can be substituted with threonine; or a vector including a polynucleotide encoding the modified polypeptide can be included.

In the present disclosure, the introduction may be performed by transformation, and the term "transformation" refers to an introduction of a gene into a host cell for the expression of the gene, but is not limited thereto. For example, the transformation may be performed using a method to introduce a vector including a polynucleotide encoding the modified polypeptide into a host cell, and the method of transforming the vector may include any method that can introduce nucleotides into cells and may be performed by selecting an appropriate standard technique known in the art. Methods such as electroporation, calcium phosphate co-precipitation, retroviral infection, microinjection, DEAE-dextran, cationic liposome, etc. may be used, but the methods are not limited thereto.

With respect to the transformed gene, both a form where the gene is inserted into the chromosome of a host cell and a form where the gene is located outside the chromosome are included, as long as the gene can be expressed in the host cell. Additionally, the gene includes DNA and RNA as a polynucleotide encoding a polypeptide, and any gene that can be introduced and expressed in a host cell can be used without limitation. For example, the gene can be introduced into a host cell in the form of an expression cassette, which is a polynucleotide construct, including all of the essential elements required for self-expression. The expression cassette may conventionally include a promoter operably linked to the gene, a transcription termination signal, a ribosome-binding domain, and a translation termination signal. The expression cassette may be in the form of an expression vector capable of self-replication. Additionally, the gene may be introduced into a host cell by itself or in the form of a polynucleotide construct and operably linked to sequences required for the expression in the host cell.

As used herein, the term "a (transformed) host cell including a vector" refers to a cell transformed with a vector which includes a gene encoding at least one target protein. In the present disclosure, any of the prokaryotic and eukaryotic microorganisms may be used as long as the microorganism can produce O-acetylhomoserine sulfhydrylase by including the vector. For example, microbial strains belonging to the genus of *Escherichia*, the genus of *Erwinia*, the genus of *Serratia*, the genus of *Providencia*, the genus of *Corynebacteria*, and the genus of Brevibacteria may be used, and *E. coli* as an example of the genus of *Escherichia*, but the microbial strains are not limited thereto.

The microorganism of the genus of *Escherichia* producing O-acetylhomoserine sulfhydrylase, which can express the modified polypeptide having an activity of O-acetylhomoserine sulfhydrylase, may include all of the microorganisms that can express the modified polypeptide by various methods known in the art, in addition to the vector introduction method described above.

Still another aspect of the present disclosure provides a method for producing methionine, using the modified polypeptide having O-acetylhomoserine sulfhydrylase activity, or a microorganism producing the modified polypeptide or culture product thereof. Specifically, the method may be a method for producing methionine, which includes reacting the modified polypeptide or a microorganism producing the modified polypeptide or culture product thereof with O-acetylhomoserine and methyl mercaptan. The methionine may be L-methionine.

The culture product of the microorganism producing O-acetylhomoserine sulfhydrylase may be prepared from culturing in a medium the microorganism producing O-acetylhomoserine sulfhydrylase, which can express the modified polypeptide having O-acetylhomoserine sulfhydrylase activity, or include the vector including a polynucleotide encoding the modified polypeptide.

As used herein, the term "cultivation" refers to growing the microorganism in an appropriately-adjusted environment. In the present disclosure, the cultivation may be performed in an appropriate medium and cultivation conditions well-known in the art. The cultivation may be easily used after adjustment according to the microbial strain being selected by one of ordinary skill in the art. The cultivation of the microorganism may be performed continuously in a batch process, continuous process, fed-batch process, etc. known in the art, but the cultivation process is not particularly limited thereto. In particular, with respect to the cultivation conditions, the pH of the culture may be adjusted to a suitable pH (e.g., pH 5 to 9, specifically pH 6 to 8, more specifically pH 6.8), by using an appropriate basic compound (e.g., sodium hydroxide, potassium hydroxide, or ammonia) or acidic compound (e.g., phosphoric acid or sulfuric acid). Additionally, during the cultivation, an antifoaming agent, such as fatty acid polyglycol ester, may be used to prevent foam generation. Additionally, the aerobic condition of the culture may be maintained by introducing oxygen or an oxygen-containing gas mixture to the culture, and the anaerobic and microaerobic states of the culture may be maintained by introducing nitrogen, hydrogen, or carbon dioxide gas to the culture without the injection of a gas. The cultivation temperature may be maintained in the range of 20° C. to 45° C., and specifically 25° C. to 40° C., but the cultivation temperature is not limited thereto. Additionally, the cultivation may be continued until the production of a useful material is obtained, and specifically for 10 hours to 160 hours, but the cultivation conditions are not limited thereto.

Additionally, as the carbon sources to be used in the culture medium, sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid) may be used alone or in combination, but are not limited thereto. As the nitrogen sources to be used in the culture medium, nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but are not limited thereto. As the phosphorus sources to be used in the culture medium, potassium dihydrogen phosphate, dipotassium hydrogen phosphate, corresponding sodium-containing salts, etc. may be used alone or in combination, but are not limited thereto. Additionally, metal salts (e.g., magnesium sulfate or iron sulfate), amino acids, vitamins, etc., which are essential growth-promoting materials, may be contained in the culture medium.

The O-acetylhomoserine may be in a purified form of O-acetylhomoserine or fermentation broth containing O-acetylhomoserine. Additionally, the methyl mercaptan may refer to a liquefied sodium methyl mercaptan ($CH_3S$—Na) form, and gaseous or liquefied methyl mercaptan ($CH_3SH$) form, as well as methyl mercaptan containing dimethylsulfide (DMS) (disclosed in International Patent Publication No. WO 2010/098629).

The method for preparing methionine can be easily determined in optimized cultivation conditions known in the art by one of ordinary skill in the art, and the method for large-scale production of methionine using the modified polypeptide and/or a microorganism producing the modified polypeptide or culture product thereof can be easily determined in optimized enzyme-activating conditions known in the art by one of ordinary skill in the art.

The method for preparing methionine may further include recovering the methionine produced in the above reaction. The recovery process may be performed using an appropriate method known in the art. For example, methods such as centrifugation, filtration, ion exchange chromatography, crystallization, HPLC, etc. may be used, but the methods are not limited thereto.

Additionally, the recovery process may include a purification step, which can be performed using an appropriate method known in the art.

DETAILED DESCRIPTION OF THE INVENTION

Hereinafter, the present disclosure will be described in detail through exemplary embodiments. However, these exemplary embodiments are provided for the purpose of illustrations only and are not intended to limit the scope of the present disclosure.

Example 1

Preparation of V196T Variant by O-acetylhomoserine Sulfhydrylase and Evaluation of their Activity

Example 1-1

Expression of O-acetylhomoserine Sulfhydrylase Derived from a Microorganism of the Genus *Rhodobacter*

The pCL-$P_{CJ1}$: metZ-rsp vector (KR Patent No. 10-1250651), in which O-acetylhomoserine sulfhydrylase derived from (a known representative microorganism of the genus *Rhodobacter sphaeroides*), was transformed into *Escherichia coli* K12 W3110 (ATCC 27325) cells by heat shock. Then, the transformants were cultured in an LB medium containing chloramphenicol (25 µg/mL). The selected colonies were inoculated into the LB medium (3 mL) and cultured at 200 rpm at 33° C. for 6 hours. The resulting culture in an amount of 250 µL was collected and re-inoculated into a fresh LB medium (25 mL in a 250 mL flask) containing chloramphenicol (25 µg/mL) and cultured at 200 rpm at 33° C. for 15 hours, and thereby wild-type O-acetylhomoserine sulfhydrylase was expressed.

Example 1-2

Preparation of V196T Variant (Novel O-acetylhomoserine Sulfhydrylase Variant)

As a position for modification to increase the activity of the wild-type O-acetylhomoserine sulfhydrylase, the 196$^{th}$ amino acid (i.e., valine) was selected.

The 196$^{th}$ amino acid, valine (Val, V), of the wild-type O-acetylhomoserine sulfhydrylase derived from *Rhodobacter sphaeroides* was substituted with threonine (Thr, T) using the Quikchange site-directed mutagenesis kit (Agilent Technologies). Specifically, a recombinant vector in which a gene encoding an O-acetylhomoserine sulfhydrylase variant was introduced was prepared by PCR reaction using the as a template along with the primers of SEQ ID NOS: 5 and 6 (Table 1).

TABLE 1

| Primer | Sequence | SEQ ID NO |
|---|---|---|
| Primer for V196T Mutant (Forward) | CTC GTC ATC GTG GAC AAT ACC TTC GCG ACG CCC GTC TTC | 5 |
| Primer for V196T Mutant (Reverse) | GAA GAC GGG CGT CGC GAA GGT ATT GTC CAC GAT GAC GAG | 6 |

Then, the introduction of the modified O-acetylhomoserine sulfhydrylase was confirmed by sequencing, and the modified O-acetylhomoserine sulfhydrylase was introduced into *E. coli* K12 W3110 by heat shock. The transformed strain was named CA05-4012 and deposited at the Korean Culture Center of Microorganisms (KCCM), an international depositary authority under the Budapest Treaty, on Nov. 27, 2014, under the accession number KCCM11611P.

The transformed *Escherichia coli* K12 W3110 was inoculated into an LB medium containing chloramphenicol (25 μg/mL) and cultured at 33° C. for 6 hours, and part of the culture was collected and transferred to an LB medium containing chloramphenicol (25 μg/mL) and cultured at 33° C. for 15 hours to induce the expression of a variant of the enzyme.

Example 1-3

Evaluation of Activity of Culture Solution of V196T Variant

2% (v/v) p-Xylene was added to the culture of the enzyme variant and the culture of the wild-type enzyme, respectively, and treated at 1,150 rpm at 33° C. for 1 hour. Then, part of each of the cultures was collected and added to a buffer (containing 50 mM potassium phosphate (pH 7.4, pH 6.4), 15 g/L O-acetylhomoserine, 0.05 mM PLP (pyridoxal 5'-phosphate), and 30 mM sodium methyl mercaptan), and reacted at 1,150 rpm at 33° C. for 5 minutes, and the reactants were subjected to HPLC analysis to measure the amount of L-methionine produced. The amount of L-methionine produced was considered as methionine conversion activity of the enzymes, and as such, the activity of the wild-type O-acetylhomoserine sulfhydrylase derived from *Rhodobacter sphaeroides* and that of the V196T variant thereof are shown in Table 2 below.

TABLE 2

| O-Acetylhomoserine Sulfhydrylase (Enzyme culture solution) | L-Methionine, pH 7.4 (g/L) | L-Methionine, pH 6.4 (g/L) |
|---|---|---|
| Wild-type | 1.10 | 0.30 |
| V196T Variant | 2.05 | 0.78 |

As a result, as shown in Table 2 above, it was confirmed that the culture solution of the variant enzyme showed a 1.86-fold increase of activity in a condition at pH 7.4 compared to that of the wild-type enzyme itself and about a 2.60-fold increase of activity at pH 6.4 compared to that of the wild-type enzyme itself.

Example 2

Purification of O-acetylhomoserine Sulfhydrylase and Evaluation of O-acetylhomoserine Sulfhydrylase Activity

Example 2-1

Purification of O-acetylhomoserine Sulfhydrylases 25 mL each of the culture solutions of wild-type O-acetylhomoserine sulfhydrylase derived from *Rhodobacter sphaeroides* and that of the V196T variant thereof obtained in Example 1 was centrifuged and the cells were collected, respectively. To prepare each cell-free extract containing O-acetylhomoserine sulfhydrylase, the cells were suspended in 15 mL of 50 mM potassium phosphate (pH 7.8) containing 150 mM NaCl and 5% glycerol and lysed using a sonicator while maintaining the cell suspension at below 10° C., respectively. Then, each cell suspension was centrifuged at 15,000×g for 25 minutes to remove cell debris. An aliquot (15 mL) of each of the cell-free extracts was loaded into 10 mL of the GE Healthcare MonoQ column, which was equilibrated with 50 mM potassium phosphate (pH 7.8) in advance, and washed/eluted in 50 mM potassium phosphate (pH 7.8) containing 800 mM NaCl by applying a gradient of 10 column volumes to the column. O-acetylhomoserine sulfhydrylase was eluted at the electrical conductivity between 15 mS/cm and 20 mS/cm. Each eluent was concentrated to a volume of 2 mL to 3 mL using the Millipore/Amicon Centricon centrifugal separator (MWCO: 3 kDa). Each concentrate was loaded into the Superdex column (HiLoad 16/600 Superdex 75 pg, GE Healthcare), which was equilibrated with 50 mM potassium phosphate (pH 7.8) containing 150 mM NaCl and 5% glycerol in advance, and separated according to the molecular weight.

O-acetylhomoserine sulfhydrylase was eluted in the form of a tetramer within 50 mL elution volume and then concentrated to a volume of 200 μL or less using the Millipore/Amicon Centricon centrifugal separator (MWCO: 3 kDa). The purity of the purified enzymes was examined by 10% SDS-PAGE gel analysis (FIG. 1) and the enzymes were stored at −80° C.

Figure 1:
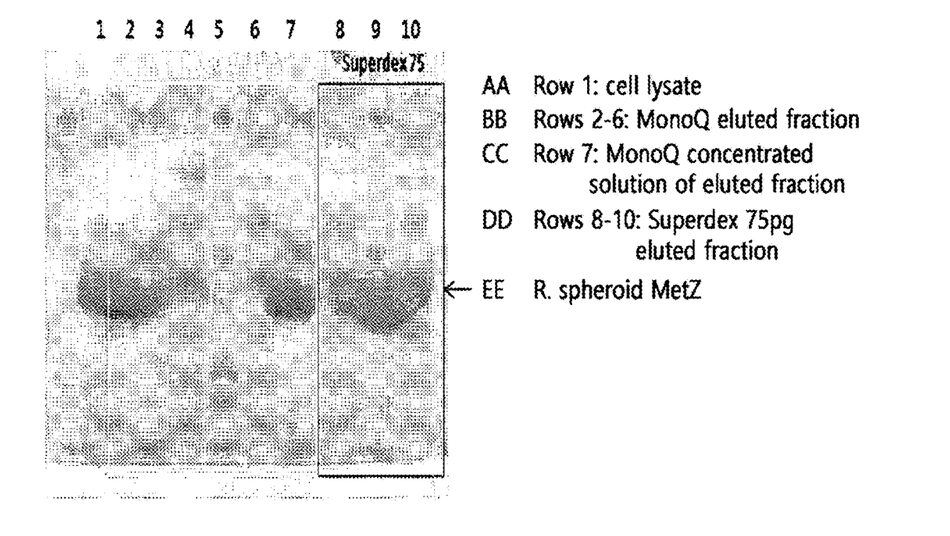
FIG. 1 shows an image illustrating the results of SDS-PAGE gel electrophoresis with regard to samples obtained in each step after the purification of the O-acetylhomoserine sulfhydrylase derived from *Rhodobacter sphaeroides*.

The results shown in FIG. 1 suggest that the variant of the present disclosure can be purified in high purity as well as being able to be overexpressed in *E. coli*.

Example 2-2

Evaluation of Activity of Purified Wild-type and V196T O-acetylhomoserine Sulfhydrylases The purified wild-type and V196T variant O-acetylhomoserine sulfhydrylases derived from *Rhodobacter sphaeroides*, each at a concentration of 1.3 mg/mL, were added into an equal amount of a buffer containing 50 mM potassium phosphate (pH 7.4 and pH 6.4), 15 g/L O-acetylhomoserine, 0.05 mM PLP (pyridoxal 5'-phosphate), and 30 mM sodium methyl mercaptan, and reacted at 1,150 rpm at 33° C. for 5 minutes. Then, the reactants were subjected to HPLC analysis to measure the amount of L-methionine produced. The activity of wild-type and V196T variant O-acetylhomoserine sulfhydrylases is shown in Table 3 below.

TABLE 3

| O-acetylhomoserine sulfhydrylase (in a purified form) | L-methionine, pH 7.4 (g/L) | L-methionine, pH 6.4 (g/L) |
| --- | --- | --- |
| Wild-type | 1.86 | 0.50 |
| V196T variant | 3.53 | 1.34 |

As a result, as shown in Table 3 above, it was confirmed that the purified variant enzyme showed a 1.90-fold increase of activity in a condition at pH 7.4 compared to that of the wild-type enzyme itself and about a 2.68-fold increase of activity at pH 6.4 compared to that of the wild-type enzyme itself.

Example 3

Evaluation of Variants where the $196^{th}$ Amino Acid of O-acetylhomoserine Sulfhydrylase is Substituted with Different Amino Acid Example 3-1

Preparation of V196S, V196L, V196D, and V196K Variants

The vectors containing the genes and *E. coli* K12 W3110 strains transformed with the vectors were prepared in the same manner as in Example 1-2, except that variants of the wild-type O-acetylhomoserine sulfhydrylase derived from *Rhodobacter sphaeroides*, in which the $196^{th}$ amino acid, valine (Val, V), of the wild-type O-acetylhomoserine sulfhydrylase derived from *Rhodobacter sphaeroides* was substituted with serine (Ser, S), leucine (Leu, L), aspartic acid (Asp, D), and lysine (Lys, K), respectively, prepared by site-directed mutagenesis as in Example 1.

Example 3-2

Evaluations of Activity of Enzyme Culture Solutions of V196S, V196L, V196D, and V196K Variants The culture solutions of variants obtained in Example 3-1 were evaluated in the same manner as in Example 1-3 and the results are shown in Table 4 below.

TABLE 4

| O-acetylhomoserine sulfhydrylase (Enzyme culture solution) | L-methionine, pH 7.4 (g/L) | L-methionine, pH 6.4 (g/L) |
| --- | --- | --- |
| Wild-type | 1.10 | 0.30 |
| V196T | 2.05 | 0.78 |
| V196S | 0.94 | 0.35 |
| V196L | 0.51 | 0.12 |
| V196D | n.d. | n.d. |
| V196K | n.d. | n.d. |

(*n.d.; none detected)

As a result, as shown in table 4 above, it was confirmed that the variants in which the $196^{th}$ amino acid was substituted with a different amino acid other than threonine showed a decrease or loss of activity.

These results suggest that the V196T variant, a novel O-acetylhomoserine sulfhydrylase variant of the present disclosure, has significantly improved enzyme activity compared to that of the wild-type and thus can be used to prepare L-methionine in an excessive amount, and in addition, the V196T variant shows a higher activity of L-methionine conversion at a lower pH and produces L-methionine in an excessive amount and thus has low activity-inhibition even at a time point when acetic acid (i.e., the final product) is accumulated thereby being able to produce L-methionine in an excessive amount. Additionally, these results suggest that L-methionine can be produced in an excessive amount even when it is purified in the form of a cell-free extract as well as an intracellular culture.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A modified polypeptide having an activity of O-acetylhomoserine sulfhydrylase, wherein the 196$^{th}$ amino acid from the N-terminus of the polypeptide represented by the amino acid sequence of SEQ ID NO: 1, valine, is substituted with threonine.

2. A polynucleotide encoding the modified polypeptide of claim 1.

3. A vector comprising the polynucleotide of claim 2.

4. A microorganism of the genus *Escherichia* producing O-acetylhomoserine sulfhydrylase, wherein the microorganism expresses a modified polypeptide having an activity of O-acetylhomoserine sulfhydrylase, in which the 196$^{th}$ amino acid from the N-terminus of the polypeptide represented by the amino acid sequence of SEQ ID NO: 1, valine, is substituted with threonine; or comprises the vector of claim 3.

5. The microorganism of claim 4, wherein the microorganism of the genus *Escherichia* is *Escherichia coli*.

6. A method for producing methionine, comprising reacting the modified polypeptide of claim 1, or a microorganism producing the modified polypeptide or culture product thereof with O-acetylhomoserine and methyl mercaptan.

7. The method of claim 6, further comprising recovering the methionine produced by the reaction.

* * * * *

SEQUENCE LISTING

```
<160> NUMBER OF SEQ ID NOS: 6

<210> SEQ ID NO 1
<211> LENGTH: 404
<212> TYPE: PRT
<213> ORGANISM: Rhodobacter sphaeroides

<400> SEQUENCE: 1

Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
            20                  25                  30
```

```
Gly Glu Met Ala Glu Ala Ile Phe Leu Thr Gln Gly Phe Val Tyr Asp
            35                  40                  45

Ser Ala Glu Gln Ala Glu Ala Arg Phe Ile Glu Thr Gly Ala Asp Glu
 50                  55                  60

Phe Ile Tyr Ala Arg Tyr Gly Asn Pro Thr Thr Arg Met Phe Glu Glu
 65                  70                  75                  80

Arg Ile Ala Ala Val Glu Gly Thr Glu Asp Ala Phe Ala Thr Ala Ser
                 85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
            115                 120                 125

Leu Glu Glu Val Leu Gly Arg Phe Gly Val Glu Val Thr Phe Val Asp
            130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
            195                 200                 205

Gly Ala Asp Val Val Ile Tyr Ser Ala Thr Lys His Ile Asp Gly Gln
            210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
            260                 265                 270

Cys Arg Ala Met Ala Asp Thr Ala Glu Lys Ile Ala Arg Ala Leu Glu
            275                 280                 285

Gly His Pro Gln Leu Gly Arg Val Ile His Pro Ala Leu Glu Ser His
            290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
            355                 360                 365

Ala Gln Lys Ala His Leu Gly Ile Thr Pro Gly Leu Val Arg Leu Ser
            370                 375                 380

Val Gly Leu Glu Asp Ala Asp Asp Leu Ile Ala Asp Leu Lys Gln Ala
385                 390                 395                 400

Leu Ala Val Ile
```

<210> SEQ ID NO 2
<211> LENGTH: 1215
<212> TYPE: DNA
<213> ORGANISM: Rhodobacter sphaeroides

<400> SEQUENCE: 2

```
atgggtatcg cgtttcgtga aggacggacg ggcatgacga aggactggaa gacaaggacg      60
caactcgtcc acgggggcag ccgccggagc cagtatggcg aaatggccga ggcgatcttc     120
ctgacccagg gcttcgtcta cgactcggcc gaacaggccg aagcgcgctt catcgagacc     180
ggcgccgacg aattcatcta tgcccgctac ggcaaccccacgacgcgcat gttcgaagag     240
cgcatcgcgg ccgtcgaggg caccgaggat gcgttcgcca ccgcctcggg catggccgcg     300
atccacggcg tgctcacctc gatcgtgcgg gcgggcgatc atctggtggc ggcgcgcgct     360
ctgttcggct cctgcatcta catcctcgag gaggtgctgg gccgattcgg cgtcgaggtg     420
accttcgtcg acggcaccga tctcgatcag tggcgcgcgg cggtgcggcc cggcacgaag     480
gccgtgttct tcgagtcggt ctcgaatccg acgctcgagg tggccgatat cggcgccatc     540
gccgagatcg cccatgccgt gggcgcgctc gtcatcgtgg acaatgtctt cgcgacgccc     600
gtcttctcga cggcggtgcg gcagggcgcg gatgtggtga tctattcggc caccaagcac     660
atcgacgggc aagggcgcgc gctcggcggc gtggtctgcg cctcgcaggc cttcatccgc     720
aaggtgctcg aacccttcat gaagcacacc ggcggctcga tgagccccttcaacgcctgg     780
ctcatgctga cgggatggc gacgctcgac ctgcgctgcc gcgcgatggc cgacacggcc     840
gagaagatcg cccgcgcgct cgagggccat ccgcagctcg gccgcgtgat ccatcccgcg     900
ctggaaagcc acccgcagca cgagatggcc aaggcgcaga tggagcgtcc cggcacgatg     960
atcgcgctcg acctcgccgg gggcaaggag gcggccttcc gcttcctcga cgccctgagg    1020
atcgtgaaga tctccaacaa tctgggcgat gcccgctcga tcgcgaccca cccggcaacg    1080
accacccacc agcgtctttc cgacgcgcag aaggcccatc tcggcatcac gcccgggctc    1140
gtgcggctgt cggtggggct cgaggatgcg gacgacctga tcgccgatct gaaacaggcg    1200
ctcgcggtga tctga                                                    1215
```

<210> SEQ ID NO 3
<211> LENGTH: 404
<212> TYPE: PRT
<213> ORGANISM: Artificial Sequence
<220> FEATURE:
<223> OTHER INFORMATION: R. sphaeroides MetZ V196T amino acid sequence

<400> SEQUENCE: 3

```
Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
        115                 120                 125
```

| Leu | Glu | Glu | Val | Leu | Gly | Arg | Phe | Gly | Val | Glu | Val | Thr | Phe | Val | Asp |
|---|---|---|---|---|---|---|---|---|---|---|---|---|---|---|---|
| | 130 | | | | | 135 | | | | | 140 | | | | |

Gly Thr Asp Leu Asp Gln Trp Arg Ala Ala Val Arg Pro Gly Thr Lys
145     150     155     160

Ala Val Phe Phe Glu Ser Val Ser Asn Pro Thr Leu Glu Val Ala Asp
    165     170     175

Ile Gly Ala Ile Ala Glu Ile Ala His Ala Val Gly Ala Leu Val Ile
   180     185     190

Val Asp Asn Thr Phe Ala Thr Pro Val Phe Ser Thr Ala Val Arg Gln
  195     200     205

Gly Ala Asp Val Val Ile Tyr Ser Ala Thr Lys His Ile Asp Gly Gln
210     215     220

Gly Arg Ala Leu Gly Gly Val Val Cys Ala Ser Gln Ala Phe Ile Arg
225     230     235     240

Lys Val Leu Glu Pro Phe Met Lys His Thr Gly Gly Ser Met Ser Pro
    245     250     255

Phe Asn Ala Trp Leu Met Leu Asn Gly Met Ala Thr Leu Asp Leu Arg
   260     265     270

Cys Arg Ala Met Ala Asp Thr Ala Glu Lys Ile Ala Arg Ala Leu Glu
  275     280     285

Gly His Pro Gln Leu Gly Arg Val Ile His Pro Ala Leu Glu Ser His
 290     295     300

Pro Gln His Glu Met Ala Lys Ala Gln Met Glu Arg Pro Gly Thr Met
305     310     315     320

Ile Ala Leu Asp Leu Ala Gly Gly Lys Glu Ala Ala Phe Arg Phe Leu
    325     330     335

Asp Ala Leu Arg Ile Val Lys Ile Ser Asn Asn Leu Gly Asp Ala Arg
   340     345     350

Ser Ile Ala Thr His Pro Ala Thr Thr Thr His Gln Arg Leu Ser Asp
  355     360     365

Ala Gln Lys Ala His Leu Gly Ile Thr Pro Gly Leu Val Arg Leu Ser
370     375     380

Val Gly Leu Glu Asp Ala Asp Asp Leu Ile Ala Asp Leu Lys Gln Ala
385     390     395     400

Leu Ala Val Ile

<210> SEQ ID NO 4
<211> LENGTH: 1215
<212> TYPE: DNA
<213> ORGANISM: Artificial Sequence
<220> FEATURE:
<223> OTHER INFORMATION: R. sphaeroides metZ V196T DNA sequence

<400> SEQUENCE: 4

```
atgggtatcg cgtttcgtga aggacggacg ggcatgacga aggactggaa gacaaggacg      60
caactcgtcc acgggggcag ccgccggagc cagtatggcg aaatggccga ggcgatcttc     120
ctgacccagg gcttcgtcta cgactcggcc gaacaggccg aagcgcgctt catcgagacc     180
ggcgccgacg aattcatcta tgcccgctac ggcaacccca cgacgcgcat gttcgaagag     240
cgcatcgcgg ccgtcgaggg caccgaggat gcgttcgcca ccgcctcggg catggccgcg     300
atccacggcg tgctcacctc gatcgtgcgg gcgggcgatc atctggtggc ggcgcgcgct     360
ctgttcggct cctgcatcta catcctcgag gaggtgctgg gccgattcgg cgtcgaggtg     420
accttcgtcg acggcaccga tctcgatcag tggcgcgcgg cggtgcggcc cggcacgaag     480
```

```
gccgtgttct tcgagtcggt ctcgaatccg acgctcgagg tggccgatat cggcgccatc      540
gccgagatcg cccatgccgt gggcgcgctc gtcatcgtgg acaataccct cgcgacgccc      600
gtcttctcga cggcggtgcg gcagggcgcg gatgtggtga tctattcggc caccaagcac      660
atcgacgggc aagggcgcgc gctcggcggc gtggtctgcg cctcgcaggc cttcatccgc      720
aaggtgctcg aacccttcat gaagcacacc ggcggctcga tgagcccctt caacgcctgg      780
ctcatgctga acgggatggc gacgctcgac ctgcgctgcc gcgcgatggc cgacacggcc      840
gagaagatcg cccgcgcgct cgagggccat ccgcagctcg gccgcgtgat ccatcccgcg      900
ctggaaagcc acccgcagca cgagatggcc aaggcgcaga tggagcgtcc cggcacgatg      960
atcgcgctcg acctcgccgg gggcaaggag gcggccttcc gcttcctcga cgccctgagg     1020
atcgtgaaga tctccaacaa tctgggcgat gcccgctcga tcgcgaccca cccggcaacg     1080
accacccacc agcgtctttc cgacgcgcag aaggcccatc tcggcatcac gcccgggctc     1140
gtgcggctgt cggtggggct cgaggatgcg gacgacctga tcgccgatct gaaacaggcg     1200
ctcgcggtga tctga                                                     1215
```

```
<210> SEQ ID NO 5
<211> LENGTH: 39
<212> TYPE: DNA
<213> ORGANISM: Artificial Sequence
<220> FEATURE:
<223> OTHER INFORMATION: Primer for V196T mutant (forward)

<400> SEQUENCE: 5
ctcgtcatcg tggacaatac cttcgcgacg cccgtcttc                              39

<210> SEQ ID NO 6
<211> LENGTH: 39
<212> TYPE: DNA
<213> ORGANISM: Artificial Sequence
<220> FEATURE:
<223> OTHER INFORMATION: Primer for V196T mutant (reverse)

<400> SEQUENCE: 6
gaagacgggc gtcgcgaagg tattgtccac gatgacgag                              39
```